United States Patent [19]

Patel et al.

[11] 4,174,355
[45] Nov. 13, 1979

[54] PROCESS FOR REMOVING α-ACETYLENES FROM DIOLEFINS

[75] Inventors: Pradeep V. Patel, Parma Heights; Donald E. Murphy, Gates Mills, both of Ohio

[73] Assignee: The B. F. Goodrich Company, Akron, Ohio

[21] Appl. No.: 916,641

[22] Filed: Jun. 19, 1978

Related U.S. Application Data

[63] Continuation-in-part of Ser. No. 770,284, Feb. 22, 1977, abandoned.

[51] Int. Cl.$^2$ ............................................... C07C 7/00
[52] U.S. Cl. ...................................... 585/843; 585/848
[58] Field of Search ................................. 260/681.5 R

[56] References Cited

U.S. PATENT DOCUMENTS

| | | | |
|---|---|---|---|
| 2,398,301 | 4/1946 | Frevel | 260/681.5 R |
| 2,408,970 | 10/1946 | Doumani et al. | 260/681.5 R |
| 3,105,858 | 10/1963 | Kresge et al. | 260/681.5 R |
| 3,202,727 | 8/1965 | Daneer | 260/681.5 R |
| 3,492,366 | 1/1970 | Winter | 260/681.5 R |
| 3,754,050 | 8/1973 | Duyverman et al. | 260/681.5 R |
| 3,897,511 | 7/1975 | Frevel et al. | 260/681.5 R |

FOREIGN PATENT DOCUMENTS 494825  7/1953  Canada ............................ 260/681.5 R

*Primary Examiner*—Delbert E. Gantz
*Assistant Examiner*—Joseph A. Boska

*Attorney, Agent, or Firm*—Alfred D. Lobo; J. Hughes Powell, Jr.

[57] ABSTRACT

Conjugated diolefins contaminated with relatively high levels of acetylenic impurities in a hydrocarbon feedstream are purified by a cyclic, vapor phase, predominantly catalytic cracking process which selectively removes alpha-cetylenes in a single pass. A feedstream containing about equal weights of isoprene and mixed monoolefins and alkanes contaminated with alpha-acetylenes including isopropenyl acetylene inter alia, up to about 5.0 percent by weight (% by wt) of the feedstream, and a larger amount of cyclopentadiene, is contacted in the vapor phase with a supported Group I B metal oxide catalyst in the absence of hydrogen, at a temperature in the range from about 300° F. to about 360° F. In this narrow temperature range, the loss of diolefin is less than 1% by weight. Essentially all the cyclopentadiene (CPD) is left unconverted. Isopropenyl acetylene content of the effluent is generally less than about 25 ppm in the single pass process which is carried out in a fixed bed reactor operating at substantially atmospheric pressure. In an analogous process, from a crude butadiene feedstream containing less than about 1.0 percent by weight of vinyl acetylene and methyl acetylene, inter alia, a butadiene effluent is recovered having less than about 200 ppm alpha-acetylenes. The butadiene effluent, substantially free from poisons for a cis-polybutadiene polymerization catalyst, except CPD, if it is present in the feed, minimizes the loss of this catalyst and provides better yields.

10 Claims, No Drawings

PROCESS FOR REMOVING α-ACETYLENES FROM DIOLEFINS

CROSS-REFERENCE TO RELATED APPLICATION

This is a continuation-in-part application of our co-pending U.S. patent application Ser. No. 770,284 filed Feb. 22, 1977, now abandoned.

BACKGROUND OF THE INVENTION

Polymer grade isoprene is obtained by purification of crude isoprene. In a petrochemical plant, crude isoprene is produced mainly as a coproduct in the production of ethylene by the cracking of naphtha, gas oil or crude oil, usually by selectively recovering a predominantly $C_5$ stream. Crude isoprene, so produced, contains acetylenic contaminants such as isopropenylacetylene (hereafter "IPEA" for brevity) and butyne-2 (hereafter "BY-2" for brevity), other pentenynes and pentadienes such as cyclopentadiene, (hereafter "CPD" for brevity), the presence of any of which, in even minute quantities, is deleterious to the polymerization of isoprene in the presence of a polymerization catalyst. Prior art processes were directed to the removal of as much of these contaminants as possible. Thus, whether the prior art process was based on hydrogenation, oxidation, hydration, adsorption or cracking, the process sought to remove acetylenic (alkyne) impurities and CPD, which individually and severally were poisons for the polymerization catalyst. Since CPD is a diolefin, a process directed to its removal also removed a significant, and economically onerous fraction of desirable diolefins. Many of the prior art processes, the most relevant of which will presently be referred to, utilize certain Group I B catalysts, and particularly cooper metal, or oxides of copper either individually or in combination with activators (promoters), over a wide range of operating conditions. Each of the prior art processes failed to recognize that the key to a successful process was to allow CPD to go unconverted, if it was present in the feed in any amount sufficient to be deleterious to the polymerization catalyst, and to remove unconverted CPD in a subsequent purification step.

One of the earliest attempts to catalytically purify conjugated diolefins contaminated with acetylenic hydrocarbons is documented in U.S. Pat. No. 2,398,301 (4/1946) to Frevel, L. K. Soon thereafter, another catalytic process, stated to be a selective hydration process, was disclosed in U.S. Pat. No. 2,408,970 to Doumani et al for the removal of acetylenic impurities in hydrocarbon mixtures containing butadiene. At present, minor quantities of IPEA, and other $C_2$–$C_5$ acetylenes are removed by selective hydrogenation of the acetylenes over a supported copper catalyst. Such processes are taught in U.S. Pat. Nos. 3,076,858 to Frevel et al; in 3,634,536 to Frevel L. K. and Dressley, L. J.; and, 3,751,508 to Fujiso et al, inter alia. Not long thereafter, an adsorption process carried out in the temperature range of 25° C.–175° C. was disclosed in U.S. Pat. No. 3,754,050 to Duyverman et al. Still more recently, U.S. Pat. No. 3,897,511 to Frevel, L. K. and Dressley, L. J., disclosed a catalytic process for removal of alpha-acetylenic impurities by their adsorption on a supported catalyst consisting essentially of a mixture of finely divided copper metal and a minor proportion of at least one polyvalent activator metal.

From a practical point of view, it is economically undesirable to hydrogenate a large feedstream of crude isoprene, no matter how selectively the hydrogenation can be effected. Until the discovery of the process of this invention the only realistic option for adequate removal of IPEA from a crude isoprene stream was by distillation wherein IPEA was removed overhead with a sacrificially large percentage of isoprene. The isoprene-rich bottoms stream containing less than 60 ppm IPEA based on isoprene content for polymer grade isoprene, and essentially all the CPD introduced in the feed stream is then distilled for removal of CPD. The process of this invention makes the sacrifice of isoprene in the overhead unnecessary.

As for a process other than selective hydrogenation for removal of acetylenic impurities from crude isoprene, it will be evident that chemisorption of the impurities on active sites, for later removal of the impurities, necessitates impractically large quantities of adsorbent, even if the adsorbent has high surface area.

It is also known that minute quantities of cyclopentadiene (hereafter "CPD" for brevity), up to about 400 ppm, may be removed from isoprene by selective adsorption of the CPD on supported copper catalysts. Such processes are taught in U.S. Pat. No. 3,492,366 utilizing a fluidized bed copper oxide catalyst in which a hydrocarbon contaminated with CPD is treated at a temperature in the range from about 0° C. to 200° C.; and British Pat. No. 1,125,520, inter alia.

It is noteworthy that, in general a supported copper oxide catalyst disclosed in U.S. Pat. No. 3,492,366 is specifically effective for the removal of CPD in amounts less than 400 ppm when the catalyst is used in a fluidized bed reactor. It has now been found that essentially the same supported cupric oxide catalysts disclosed therein as being so effective for the removal of CPD, are effective in the process of this invention to allow the CPD, if present, to go essentially unconverted. This catalyst was demonstrated in U.S. Pat. No. 3,492,366 to be unexpectedly unable to perform as well in a fixed bed reactor. The peculiar and unexplained preference of a catalyst for CPD adsorption in one reactor over another apparently analogous one, though only the type of bed in the reactor waschanged in this particular process, is further evidence that a particular combination of process conditions is critical when Group I B metal oxide catalysts are used in any practical process for purifying diolefins. This criticality in a practical process is generally reflected and focussed by the absence of examples disclosing mass balances and analyses of the effluent in other relevant prior art disclosures relating to conversion of impurities in the absence of hydrogen.

Polymer grade butadiene for the cis-polybutadiene polymerization system is obtained by purification of butadiene containing unacceptably high levels of apha-acetylenes such as vinyl acetylene and methyl acetylene. U.S. Pat. No. 3,897,511 teaches the selective chemisorption of alpha-acetylenes on copper catalysts activated with NiO, CoO, CrO or MnO. The activated copper catalyst is reduced with hydrogen prior to use. British Patent No. 1,291,397 teaches a mixed CuO/ZnO catalyst which can also be used for chemisorption of alpha-acetylenes.

The prior art is replete with a multiplicity of hydrogenation catalysts particularly suited for hydrogenation of acetylenic and other impurities in conjugated diolefin streams. A few of these catalysts are said to effectively lower the final acetylenic concentration of a feedstream from 1 percent to below 100 ppm without excessive conversion of the diene to a monoolefin or alkane, but the period of time over which the activity can be maintained is quite unpredictable. For one reason or another, some hydrogenation catalysts make for more successful hydrogenation processes than others, and the search for economically competitive processes, whether by hydrogenation or not, continues unremittingly.

Relatively little interest has been directed to the conversion of alkynes by contact with base metal oxide catalysts without hydrogenation or hydration of the alkynes. Catalysts consisting of finely divided copper alone or mixed with an activator metal were known to be useful for removal of the alkynes by selectively decomposing or polymerizing these contaminants, but such a process, inter alia, was known to be subject to one or more disadvantages, as specifically stated in aforementioned U.S. Pat. No. 3,897,511, column 1, lines 26–43. As stated in the earlier Frevel U.S. Pat. No. 2,398,301, temperatures above 200° C. (392° F.) were indicated, 275° C. (527° F.) to 325° C. (617° F.) being preferred (page 2, right hand column, line 38). At these relatively higher temperatures, higher than 300°–360° F., not only alpha-acetylenes but also CPD is removed, and unavoidably, as evidenced by the exothermic reaction noted, a sufficiently large proportion of desirable diolefins are converted to mask the endothermic cracking of acetylenic impurities. We are unaware of any prior art which teaches conversion of acetylenic impurities and their removal by the use of a supported copper oxide or silver oxide hydrogenation catalyst, in the absence of hydrogen, in a predominantly catalytic cracking process.

SUMMARY OF THE INVENTION

A cyclic vapor phase process has been discovered for the purification of crude conjugated diolefins wherein acetylenic impurities are selectively removed without supplying hydrogen or oxygen to the reactor in which the process is carried out. The process provides the immediate benefits of not utilizing hydrogen. This process, because it can utilize a crude diolefin feed, avoids undue sacrifice of diolefins in a prior distillation step to prepare the feed. This process makes it economically practical to treat and suitably purify a crude conjugated diolefin feed, having four to five straight chain, or cyclic, carbon atoms, for use in a polymerization system, without debilitating conversion losses of valuable feed components; and, to treat a relatively refined diolefin feed if such is available, more effectively.

More particularly, a crude isoprene feedstream containing up to about 0.1 percent by weight of isopropenyl acetylene and other alpha-acetylenes, and more than about 0.5 percent by weight of cyclopentadiene is contacted in the vapor phase with a supported cupric oxide or silver oxide catalyst, in a fixed bed reactor, in the absence of added hydrogen or oxygen. The alpha-acetylenes in the reactor effluent are removed to a level less than about 20 ppm by weight of effluent in a single pass, without substantially lessening the concentration of CPD. The crude isoprene feed may, optionally, be supplemented with diluent gas including an inert gas and steam. The crude isoprene feed is contacted continuously with the fixed bed catalyst for about 24 hours to about 72 hours at a temperature in the range from about 300° F. to about 360° F. The feed is then discontinued, the catalyst is regenerated in a conventional manner, and the reactor readied for reintroduction of the feed, thus providing a cyclic, vapor phase process. Unconverted CPD in the effluent is removed by a subsequent fractional distillation step.

In an analogous process, crude butadiene contaminated with up to about 1.0 percent of vinyl acetylene and methyl acetylene is contacted in the vapor phase with a supported cupric oxide or silver oxide catalyst, in a fixed bed reactor, in the absence of added hydrogen or oxygen. The alpha-acetylenes are removed to a level less than about 200 ppm by weight of effluent, in a single pass without signficant loss of diolefins. The feed may optionally be supplemented with a diluent gas, including an inert gas and steam. The crude butadiene stream is contacted continuously with the fixed bed catalyst for about 24 hours to about 72 hours at a temperature in the range from about 300° F. to about 360° F. The feed is then discontinued, the reactor is regenerated in a known manner, and the reactor readied for reintroduction of the feed.

Whether the process of this invention is used to purify isoprene or butadiene by removal of contaminant acetylenic impurities, the purification is effected with less than 1% by weight loss of diolefins and essentially all CPD in the feed is unconverted. Quite surprisingly, conversion of acetylenic impurities is lower, and loss of diolefins fed is greater, when the supported cupric oxide or silver oxide catalyst is promoted with elements from Group VI and Group VIII of the Periodic Table.

Where a relatively refined feedstream of isoprene or butadiene is available, in which deleterious alpha-acetylene impurities are present in relatively low concentrations compared to their concentrations in a crude feedstream, the process of this invention makes it possible to remove these impurities to a low level sufficient to provide an effluent which can effect a polymerization catalyst savings of 50 percent or more, when the effluent, after a subsequent fractionation to remove unconverted CPD, is used in a synthetic natural rubber or polybutadiene polymerization system.

DETAILED DESCRIPTION OF PREFERRED EMBODIMENTS OF THE INVENTION

Isoprene, which is typically present in an amount less than about 50% by weight in a $C_5$ fraction from a naphtha cracking furnace, contains acetylenic IPEA, BY-2 and diolefinic CPD in minor amounts. In addition there may also be present minor amounts of (a) piperylenes, (b) other $C_5$ compounds such as 2-methyl butene-1, (hereinafter "2-MB-1"), and 2-methyl butene-2, (hereafter "2-MB-2"), and, (c) other alpha-acetylenes such as trans-3-pente-1-yne (hereafter "t-PEY"), cis-3-penten-1-yne (hereafter "c-PEY"), and 1,4-Pentenyne (hereafter "1,4-PEY"). Pentenynes may be present in a concentration as high as about 0.1 percent.

Crude butadiene, such as is typically used to furnish feedstock for a cispolybutadiene catalytic polymerization system contains vinyl acetylene (hereafter "VA"), ethylacetylene (hereafter "EA"), and methylacetylene (hereafter "MA") in minor amounts which are deleterious to the system, and varying amounts of other impurities such as propadiene, lower paraffins, lower alkyenes and the like which are not harmful.

The present process, in its most preferred embodiment, comprises contacting a feedstock of conjugated diolefin contaminated with acetylenic impurities, with a solid Group I B metal oxide catalytic cracking catalyst at an elevated temperature in a reactor, at or near atmospheric pressure, and recovering an effluent in which alpha-acetylenic impurities have selectively been converted to compounds not harmful in a subsequent polymerization of the diolefin, but in which CPD, if present, is left unconverted. This process relies for its effectiveness upon the use of several critical process conditions. These conditions are as follows: (i) a cupric oxide cracking catalyst having more than 10% but less than 25% by weight cupric oxide in a fixed bed reactor, which cracking does away with a separate desorption step, (ii) a narrow temperature range of from 300° F. to 360° F. in which the catalyst is surprisingly selective, (iii) no hydrogen or oxygen as feed to the reactor, (iv) a relatively high gas hourly space velocity (GHSV) of feed, in the range from about 100 to about 1500 GHSV which results in (v) essentially no conversion of CPD if it is present in the feed, (vi) at least 90% by weight conversion of the alpha-acetylenic impurities in the feed, and, (vii) less than 1% by weight loss of diolefins fed to the reactor.

The presence of saturated hydrocarbons, and particularly butanes and pentanes in the feed, does not appear to influence the conversion of alpha-acealkanes and the like, but appear to act only as diluents. Similarly, other inert gaseous diluents such as nitrogen, the oxides of carbon, and steam, may be present in the feed to the reactor without deleterious effect. No substantial improvement in conversion is observed when this process is carried out in the presence of a diluent, compared to a process under similar conditions, in the absence of a diluent; from an operating point of view it is preferred to keep diluents to a minimum. However, the commercial desirability of the process of this invention is based on the fact that, despite the presence of relatively large proportions of these diluent saturated hydrocarbons, the conversion of alpha-acetylenes is effected with surprising effectiveness and selectivity. The excellent selectivity of the process which limits the loss of diolefins in the feed to less than 1% by weight at 90%, or better, yet effect the conversion of alkynes, is corroborated by evidence that this process is not exothermic but endothermic. As is well known, an exothermic reaction which results in the removal of alkynes is indicative of a high level of conversion of diolefins, sufficient to mask the conversion of alkynes which is endothermic.

Only the oxides of copper and silver in the highest oxidation state, on a suitable catalyst support, will function in the conversion of alpha-acetylenes to compounds which will not adversely affect catalysts used in the polymerization of isoprene and butadiene. The oxides used are cupric oxide (CuO) and silver oxide ($Ag_2O$) supported on a catalyst support. Cupric oxide is most preferred for economical reasons. Unsupported cupric oxide catalyst is ineffective in this process, as is copper metal. The supported catalyst preferably contains from about 75 percent to about 90 percent by weight of a porous catalyst support and preferably from between about 80 percent to about 95 percent. A nonporous catalyst is effective for too short a period to be deemed economical in a commercial process. Any known catalyst support such as alumina, pumice, silicon carbide, zirconia, titania, alumina-silica, and the inorganic phosphates, silicated aluminates, borates and carbonates, stable under the reaction conditions, may be used, but those with relatively high (BET) surface area of at least 10 sq. meters/gm and high pore volume of at least 0.1 cc/gm are preferred. Most preferred is gamma-alumina having a surface area in excess of 100 $m^2/gm$, a pore volume in excess of 0.5 cc/gm and an average pore diameter greater than about 100 Å.

The supported catalyst may be prepared by any one of numerous methods of catalyst preparation known to those skilled in the art. The preferred manner of arriving at the oxides of the instant catalyst is by use of the water-soluble salts of copper and silver, from which the oxides are precipitated in situ. The supported catalyst's activity is enhanced by heating the catalyst at an elevated temperature. Preferably, the catalyst is heated at a temperature in the range from about 550° F. to about 800° F. for from about 2 hours to about 24 hours. If activity is insufficient, the catalyst can be heat-treated at even a higher temperature than 800° F. but well below a temperature deleterious to the catalyst, that is, a temperature at which the catalyst is deactivated, melted or decomposed.

A wide range of particle sizes for the supported oxide catalyst may be used, depending in part upon process conditions dictated by the choice of a fixed bed reactor. In this process, a fluidized bed of catalyst is of no particular advantage over a fixed bed. Accordingly relatively large particles of catalyst are preferred, the particular size being chosen with due regard for pressure drop and heat transfer considerations. A preferred particle size is in the range from about 25 U.S. Standard mesh to about ½ inch.

Excellent results are obtained whether the essential catalytic ingredient of the supported catalyst is cupric oxide or silver oxide. Since cupric oxide is more economical than silver oxide, particular reference herein is to cupric oxide, it being understood that silver oxide may be substituted for cupric oxide, or a mixture of cupric oxide and silver oxide may be used.

To provide an economical process it is critical that the concentration of cupric oxide be in the range from 10 but less than 25 percent by weight of supported catalyst. Several suitable porous supported cupric oxide catalysts are presently commercially available. Of particular interest are Dow K catalyst obtained from Dow Chemical Co. and T-315, T-317, T-366, and T-1990 catalysts obtained from the Girdler Chemical Dept. of Chemetron Corp. Most preferred is the T-1990 catalyst.

It is essential in this process to contact the supported cupric oxide catalyst with the impure diolefin feedstream in a narrow temperature range of about 300° F. to about 360° F., in which range the feed is in the vapor phase, the alkynes are converted, but CPD and other diolefins are not. The pressure at which the reaction is carried out is not critical, the conversion being substantially the same over a wide range. It will thus be apparent that there is no economical advantage to carrying out the reaction at substantially elevated pressures. Preferred operating pressures are near-atmospheric, that is, in the range from about 10 psia to about 30 psig. Even higher pressures up to about 200 psig may be used which have the advantage of more efficient product recovery, but such higher pressures are generally economically unjustifiable. No oxygenated organic compounds such as aldehydes and ketones are formed in the process. This evidence indicates that the process is not an oxidation process.

Only a brief apparent contact time with the catalyst is required for effective removal of the alpha-acetylenic impurities. The apparent contact time is defined as the length of time in seconds which a unit volume of gas, measured under the conditions of reaction, is in contact with the apparent unit volume of catalyst. The apparent contact time may be calculated, for instance, from the apparent volume of the catalyst bed, the average temperature and pressure of the reactor, and the flow rates in the reactor of the gaseous feed components. The optimum contact time in the range from about 1 sec to about 30 secs, will depend on the diolefin being purified, the amount of diluent, and the concentration of impurities to be removed. The generally short contact time is significant, as it is deemed to support the hypothesis that alpha-acetylenic impurities are not merely adsorbed on the catalyst for later removal during the regeneration of the catalyst, but are chemisorbed on the catalyst and converted by cracking to other compounds. This hypothesis is substantiated by the relatively small number of active sites available on the catalyst in relation to the number of molecules of alpha-acetyles converted. Experimental results indicate that more than about 0.202 g of alpha-acetylenes may be removed per g of supported catalyst. This is 164 times the calculated theoretical amount of alpha-acetylene which may be removed by chemisorption alone. The catalyst is said to demonstrate a "turnover number" of 164. In general, the process of this reaction allows the catalyst to demonstrate a turnover number in the range from about 100 to about 300 which characterizes the reaction as a predominantly catalytic cracking reaction.

After a period of about 36 hours on stream, the feed is discontinued, as is any diluent gas, if used. The reactor is then heated to a regeneration temperature in the range from about 600°–800° F. and the catalyst is regenerated with steam and a molecular oxygen containing gas, preferably air. There is no visual indication of any substantial reduction of the copper oxide prior to regeneration of the catalyst. When regeneration of the catalyst is complete, the reactor is readied for reintroduction of feed.

The precise period of onstream time in the catalytic conversion cycle of this vapor phase process will depend upon the size of the fixed bed, the level of contaminants in the feed, the flow rate through the reactor, the specific concentration of cupric oxide on the particular catalyst support used, the temperature at which the reactor is operated, and other factors.

In the examples hereinbelow, flow rates are measured as the gas hourly space velocity, or GHSV, which is defined as the volumes of gaseous component contacted at about 25° C. and at a pressure of about one atmosphere per volume of the solid catalyst particles per hour. All "percent" references are to percent by weight, unless otherwise specified.

EXAMPLE 1

A tubular reactor was packed with about 150 cc of 0.125 in. (nominal size) pellets of a catalyst comprising about 14 percent by weight cupric oxide on gamma alumina (T-1990 catalyst obtained from Girdler Chemicals Dept. of Chemetron Corp.) The reactor was packed by tapping it lightly to form a fixed bed. The reactor was heated and maintained at a temperature in the range from about 320° F. to about 340° F. at atmospheric pressure. The catalyst has a surface area of about 200 sq meters/g, a pore volume of 0.54 cc/g, an average pore diameter of 133 A and a bulk density of 35 lbs/ft$^3$.

In a specific run a fixed bed of the Girdler T-1990 catalyst is formed with 150 cc. of the catalyst lightly packed in a tubular reactor. The feed was a crude, isoprene stream which, upon analysis, contained 46.92% isoprene, 0.83% CPD, 0.58% BY-2, 808 ppm IPEA, 125 ppm cis-3-PEY-1, 181 ppm 1–4 PEY, and 2 ppm trans-3 PEY-1. The run lasted 36 hours and only hydrocarbon vapor contacted the catalyst. The temperature of the reactor was 350° F., which temperature was maintained by electrical heating means. It was evident from the amperes drawn by the heater, that heat is provided to the reactor during the run. Also, the feed is pretreated at 360° F. before being introduced into the reactor. The concentration of IPEA in the effluent is stated to be less than 50 ppm, though it was consistently much lower than 50 ppm. Precise measurement of IPEA concentrations in the effluent were not made because of difficulty in obtaining measurements in the 1–15 ppm range. Essentially all the pentenynes are removed. Except for a little initial adsorption of CPD, essentially all the CPD remains unconverted in the effluent.

TABLE I

| Time on Stream (hrs) | Hydrocarbon GHSV | Effluent Analysis | | | | Conversion | | | IP Loss % |
|---|---|---|---|---|---|---|---|---|---|
| | | % IP | % BY-2 | IPEA ppm | % BY-2 | % CPD | % IPEA | | |
| 4 | 310 | 46.93 | 0.53 | 50 | 4 | 9 | 94+ | | 0.0 |
| 8 | 325 | 46.33 | 0.31 | 50 | 47 | 9 | 94+ | | 1.2 |
| 12 | 245 | 46.75 | 0.56 | 50 | 4 | 2 | 94+ | | 0.4 |
| 16 | 202 | 46.65 | 0.61 | 50 | 4 | 3 | 94+ | | 0.6 |
| 20 | 401 | 46.94 | 0.66 | 50 | 0 | 0 | 94+ | | 0 |
| 24 | 344 | 47.00 | 0.55 | 50 | 5 | 0 | 94+ | | 0 |
| 28 | 242 | 47.04 | 0.56 | 50 | 4 | 0 | 94+ | | 0 |
| 31 | 299 | 46.71 | 0.63 | 50 | 0 | 0 | 94+ | | 0.4 |
| 34 | 305 | 46.69 | 0.61 | 50 | 0 | 0 | 94+ | | 0.5 |
| 36 | 440 | 47.20 | 0.61 | 50 | 0 | 0 | 94+ | | 0 |

In several additional runs, a crude isoprene feed stream comprising C$_5$ alkanes, isoprene 47.28%, cyclopentadiene (CPD) 0.8%, butyne-2 (BY-2) 0.5%, isopropenyl acetylene (IPEA) 864 ppm, varying amounts of piperylenes and C$_5$ alkenes, and small amounts of pentenynes, is vaporized and introduced at about 320° F.–340° F. to the reactor, near the top. The rate of flow of crude isoprene is in the range from about 280 GHSV to about 440 GHSV. Dry nitrogen gas may also be introduced as a diluent to obtain better reactor operation. If N$_2$ is used, it is introduced at a rate in the range from about 75 GHSV to about 140 GHSV, at a temperature in the range from about 320°–340° F., preferably intermixed with the crude isoprene.

The data for the several runs, each lasting for 35.5 hours is summarized in Table II herebelow:

TABLE II

| | |
|---|---|
| Time on stream, hours | 35.5 |
| Pressure, psia | 14.7 |
| Temperature, °F. | 320–340 |
| Crude Feed, GHSV | 280–440 |
| Isoprene loss, % | 0–0.9* |
| IPEA conversion, % | 90–100 |
| CPD conversion, % | 0–2 |
| BY-2 conversion, % | 4–7 |

*average loss for the run is 0.2%

The concentration of IPEA in the effluent from the reactor, near the end of each run, is generally less than about 50 ppm. The run may be prolonged until the concentration reaches or even exceeds 50 ppm depending upon what further purification of the effluent is to be practiced; for example, if a subsequent distillation of the effluent to remove the CPD also removed IPEA, a run may be prolonged until concentration of IPEA approaches 100 ppm. However, if the further purification steps chosen do not remove the IPEA then a run is desirably terminated when the IPEA concentration is less than, or equal to about 50 ppm. When the run is terminated, the feed to the reactor is discontinued and the porous supported catalyst is regenerated, for example, by contacting the catalyst with air and steam at an elevated temperature for a sufficient period of time to restore the catalyst to its initial activity level.

Analyses of the effluents from each run indicated that conversion of alpha-acetylenes were higher in the early part of the run and gradually diminished as the run progressed. Alpha-acetylenes other than IPEA were present in the effluent in so small a concentration as to be disregarded. A run was discontinued when the level of IPEA in the effluent reached 50 ppm. A concentration of IPEA in excess of about 60 ppm in the isoprene feed to a synthetic natural rubber polymerization system generally causes unacceptably high catalyst loss and low yields.

The concentration of CPD in the effluent is found to be initially lowered indicating some removal of CPD by the fixed bed catalyst. However, the concentration of CPD in the effluent rapidly approaches that of the feed, and it is apparent that after initial adsorption of CPD on the catalyst's available sites, there is little further activity of the catalyst with respect to conversion of CPD. This adsorption of CPD, because it occupies available sites, is particularly evident when CPD is present in the feed in a relatively high concentration of more than about 500 ppm. Since the conversion of alpha-acetylenes and particularly IPEA, appears to be independent of the concentration of CPD in the feed stream, and consequently, of the adsorption of CPD on the catalyst, it appears that the sites occupied by adsorbed CPD are different from the active sites on which the alpha-acetylenes are chemisorbed and, it is hypothesized, selectively cracked. This chemisorption and selective cracking of alpha-acetylenes, in the absence of added hydrogen, produces lower hydrocarbons in the effluent. It is this peculiar and unexpected behavior of the known supported catalysts which makes the process of this invention effective for the removal of alpha-acetylenes. As will be seen from the following example, alpha-acetylenes in an amount less than about 500 ppm in a relatively refined isoprene feed are essentially completely removed from the effluent.

EXAMPLE 2

A relatively refined isoprene feedstream is treated in a manner analogous to that described in example 1 hereinabove. A tubular reactor is packed with a fixed bed of a catalyst comprising about 14 percent CuO by weight, on gamma alumina (T-1990 Girdler catalyst used in previous example) which is essentially free of $Na_2O$. The reactor is heated and maintained at a temperature in the range from about 320° F. to about 340° F. at atmospheric pressure. The refined isoprene feed stream comprising $C_5$ alkanes, IPEA 152 ppm, lesser concentrations of other alpha-acetylenes impurities, piperylenes and 92 ppm CPD, is vaporized and introduced at about 340° F.–360° F. to the reactor, near the top. The rate of flow of feed is the range from about 100 GHSV to about 200 GHSV. The data for several runs, each lasting for about 35.5 hours is summarized in Table III herebelow:

TABLE III

| | |
|---|---|
| Time on stream | 35.5 hours |
| Pressure, Psia | 14.7 |
| Temperature, °F. | 340–360 |
| Crude feed, GHSV | 100–200 |
| IP loss (%) near end of run | less than 1% |
| IPEA conversion (%) near end of run | 95 |
| CPD conversion (%) near end of run | 10% |

As will be evident from Table III, conversion of IPEA was essentially complete even near the end of a run, while CPD is essentially unconverted. The measured 10% conversion of CPD is due mainly to chemisorption, and active sites are available because the CPD concentration in the feed is only 92 ppm and the adsorption capacity of the catalyst is not exhausted. Clearly, where the initial concentration of IPEA in the feed is relatively low, the vapor phase conversion cycle of the reactor may be much longer than when the concentration is in excess of about 500 ppm. As before, alpha-acetylenes other than IPEA were present in too small a quantity to be of significance.

It will also be evident that a concentration of 92 ppm CPD is too high to be removed sufficiently so as to produce directly an effluent suitable for a synthetic natural rubber polymerization system; and, that to produce an effluent containing less than about 3 ppm CPD, utilizing this process, it will be desirable not to use a refined feedstream containing substantially more than 3 ppm CPD, even if it contains a concentration of alpha-acetylenes which can be removed. Stated differently, if the feed to this process contains more than about 3 ppm CPD, a subsequent purification step will be necessary to provide removal of the unconverted CPD in the effluent.

EXAMPLE 3

Crude butadiene, obtained as a $C_4$ cut from cracking furnaces used for the production of ethylene, is treated in the vapor phase in the absence of added hydrogen, in a manner analogous to that described in Examples 1 and 2 hereinabove:

A typical, average crude butadiene feedstream analysis is as follows:

| Component | Percent |
|---|---|
| n-butene | 18.2 |
| isobutene | 28.3 |

-continued

| Component | Percent |
|---|---|
| butene-2 cis and trans | 10.2 |
| butadiene 1-3 | 38.8 |
| butadiene 1-2 | 0.1 |
| propane and propylene | 0.3 |
| $C_4$ paraffins | 2.7 |
| ethylacetylene | 0.3 |
| vinylacetylene | 0.5–1.0 |
| propadiene | 0.1 |
| methyl acetylene | 0.1 |

In specific runs, a tubular reactor was packed with T-1990 catalyst pellets, as in Examples 1 and 2, to form a fixed bed of about 100 cc. The reactor is heated and maintained at a temperature of about 320° F. to about 340° F. at atmospheric pressure. The runs lasted 24 hours at an average GHSV in the range from about 500 to about 1000. The effluent analysis indicated that concentration of VA and MA at the end of 24 hours is about 200 ppm and 50 ppm respectively. Butadiene loss at reactor operating conditions is generally less than 0.5%, and, near the end of a run, may be in the range from about 0.5% to about 1.0%. The reactor may be operated at a higher temperature in the range from about 360° F. to about 400° F., and even as high as 600° F., but higher temperatures than about 360° F. are uneconomical because of losses of diolefins. Better conversions of VA and MA are obtained at lower space velocity and a low GHSV in the range from about 200 to about 400 may reduce MA concentration in the effluent to about 10 ppm. A run is terminated when a preselected desirably low concentration of alpha-acetylenes in the effluent, typically about 200 ppm, is exceeded.

The choice of reactor operating conditions to produce, directly, an effluent butadiene stream which can effect desirable savings in catalyst consumption in a polybutadiene polymerization system depends on several factors. Among these factors are the initial concentrations of alpha-acetylenes in the crude feedstream, the cost of reactor operation, and the reduction of catalyst consumption effected by the purity of the effluent. To illustrate, a typical butadiene effluent may be bottle polymerized to produce polybutadiene with half the amount of a conventional catalyst if the alpha-acetylenes are reduced from 400 ppm to 100 ppm.

As in Examples 1 and 2 hereinabove, when the purification portion of the run is terminated, the catalyst in the reactor is conventionally regenerated as described, and readied for another operating cycle.

EXAMPLE 4

A relatively refined butadiene feedstream is treated in a manner analogous to that described in Example 3 hereinabove. In a specific run, a tubular reactor was packed with a fixed bed of catalyst consisting essentially of about 14 percent CuO (T-1990 Girdler catalyst on a porous gamma-alumina support). The reactor is heated and maintained at a temperature of about 300° F. at atmospheric pressure. The butadiene feedstream contasminated with 262 ppm vinyl acetylene (VA) and 10 ppm methyl acetylene (MA), is vaporized and introduced near the top of the reactor at a GHSV of 1000. Analyses of samples taken at intervals during the run are set forth in Table IV herebelow:

TABLE IV

| Time on Stream (hours) | Effluent analyses | |
|---|---|---|
| | VA, ppm | MA, ppm |
| 2 | 2 | 1 |
| 6 | 2 | 1 |
| 12 | 2 | 2 |
| 18 | 2 | 2 |
| 21 | 14 | 5 |
| 24 | 14 | 10 |

It is noted that at the end of the run VA is still being converted, but MA is no longer removed. Measurements for losses due to conversion of butadiene indicated that at no time did the conversion of butadiene exceed 1%.

EXAMPLE 5

A crude isoprene feedstream is treated in a manner analogous to that described in Example 1 hereinabove, by contacting it with a fixed bed of Girdler T-315 supported cupric oxide catalyst. There is no added hydrogen or oxygen fed to the reactor. The chromatographic analysis of the crude isoprene, over a retention time of about 108.5 minutes is presented herebelow in Table V.

TABLE V

| Time (min) | Relative Ret Time | Conc (%) | Component |
|---|---|---|---|
| 6.99 | 0.000 | 0.0073 | $CH_4$ |
| 7.43 | 0.015 | 0.0066 | $C_2H_6, C_2H_4$ |
| 8.47 | 0.052 | 0.0021 | $C_3H_8$ |
| 9.98 | 0.106 | 0.0004 | iso-butane |
| 11.42 | 0.157 | 0.0006 | n-butane |
| 11.88 | 0.174 | 0.0004 | neopent |
| 13.87 | 0.244 | 0.0015 | Be-1 |
| 14.38 | 0.262 | 0.0007 | isobutene |
| 16.43 | 0.335 | 0.0396 | MB + 1-Be-2 |
| 17.38 | 0.369 | 0.0833 | C-Be-2 |
| 19.50 | 0.445 | 3.7670 | 3-MB-1 + npent |
| 22.00 | 0.534 | 0.0371 | BD |
| 25.44 | 0.656 | 13.1528 | Pe-1 |
| 28.57 | 0.767 | 14.4768 | 2-MB-1 |
| 29.70 | 0.808 | 5.9224 | t-Pe-2 |
| 31.41 | 0.869 | 3.6732 | C-Pe-2 |
| 34.01 | 0.961 | 3.8793 | 1,4 P = D |
| 35.09 | 1.000 | 3.1690 | 2-M B-2 |
| 39.61 | 1.160 | 0.0066 | hexane |
| 41.86 | 1.240 | 0.0018 | By-1 |
| 53.54 | 1.656 | 46.4544 | isoprene |
| 66.59 | 2.120 | 0.9251 | t-pip |
| 68.76 | 2.198 | 0.5403 | By-2 |
| 73.10 | 2.352 | 0.1805 | C-pip |
| 90.95 | 2.987 | 0.7821 | CPD |
| 96.51 | 3.185 | 0.0245 | Py-1 |
| 100.32 | 3.321 | 0.0010 | unknown |
| 108.48 | 3.611 | 0.0921 | IPEA |

In this run which was made over a period of 5 days and spanned a period of about 36 on-stream hours, numerous chromatographic analyses of the effluent were made. The average analysis of the effluent over the entire run is set forth hereinbelow:

TABLE VI

| Component | % concentration |
|---|---|
| Methyl-butene | 0.745 |
| 3-methyl-butene-1 | 3.77 |
| n-pentane | 0.97 |
| pentene-1 | 13.57 |
| 2-methyl-butene-1 | 13.17 |
| trans-pentene-2 | 6.75 |
| cis-pentene-2 | 4.67 |

TABLE VI-continued

| Component | % concentration |
|---|---|
| 2-methyl-butene-2 | 4.85 |
| Isoprene | 46.31 |
| Butyne-2 | 0.52 |
| trans-piperylene | 1.78 |
| cis-piperylene | 0.62 |
| CPD | 0.72 |
| IPEA (ppm) | 50* |

*near end of run exceeds 50 ppm but less than 100 ppm.

It is evident from the foregoing analyses that essentially no ketones, aldehydes or other oxygen-containing organic compounds are formed during the reaction. An examination of the catalyst, after the run was terminated, indicates no visual evidence of metallic copper being formed.

To determine the "turnover number" for Girdler T-1990 catalyst which consists essentially of cupric oxide supported on porous gamma alumina, a "synthetic" feed was prepared having the following composition:

| 2-methyl-butene-2 | 95.1168% |
|---|---|
| IPEA | 4.2262% |
| Isoprene | 0.1039% |

This feed was contacted with 100 cc T-1990 catalyst in a fixed bed maintained at about 16 hours at an average hydrocarbon VVH of about 300 and 16 successive analyses were made over the period. The cumulative weight of IPEA removed by the catalyst at the end of the run was 11.11 g.

Calculation of Turnover Number:

Assuming that cupric oxide is supported on all active sites ($0.3 \times 10^{13}$ per cm$^2$), and that each active site can chemisorb 2 molecules of IPEA (see Mann, R. S. and Khulbe, K. C., J. Catalysis, 42, 115–121), the capacity of the catalyst is $0.124 \times 10^{-2}$ g of IPEA per g of catalyst.

IPEA removed in run =
$$\frac{11.11 \text{ g}}{100 \text{ cc} \times 0.55 \text{ g/cc}} = 0.202 \text{ g/g of catalyst}$$

Turnover Number = Ratio of IPEA removal (Experimental/theoretical) = 164.

In the claims below, the term "consisting essentially of" is meant to include the essential catalytic ingredient, namely cupric oxide, or silver oxide, or mixtures thereof, but is not meant to exclude small amounts of other elements the presence of which may be incident to the quality, origin, or particular processing of raw materials used to manufacture the supported catalyst.

From the foregoing description of the manner in which the experimental runs were made, it will be apparent that there were no provisions for many process steps which would be engineered into a commercial unit.

We claim:

1. A process for removing alpha-acetylenes from a hydrocarbon vapor mixture comprising said alpha-acetylenes and a conjugated diolefin having four to five carbon atoms, which process comprises, (a) introducing only said hydrocarbon vapor mixture optionally with an inert gaseous diluent, to a fixed bed reactor without supplying hydrogen or oxygen thereto, (b) contacting said mixture at a temperature in the range from about 300° F. to about 360° F. with a solid porous supported catalyst selected from the group consisting essentially of supported cupric oxide and silver oxide in the range from more than 10% but less than 25% by weight of said catalyst, at a gas hourly space volocity (GHSV) in the range from about 100 to about 1500, (c) cracking said alpha-acetylenes to non-oxygenated organic compounds so as to produce at least 90 percent conversion of said alpha-acetylenes in the effluent from said reactor, in which effluent cyclopentadiene, if present in the feed, is essentially unconverted, with loss of diolefin to less than 1 percent by weight of the hydrocarbon feed, and (d) providing heat to said reactor so as to maintain said temperature range during said process.

2. The process of claim 1 wherein said alpha-acetylenes in said mixture are present in an amount up to about 5.0 percent by weight of said mixture, and said alpha-acetylenes in said effluent are present in an amount less than about 50 parts per million parts (ppm) by weight of said mixture.

3. The process of claim 2 wherein said porous catalyst support is gamma alumina and said alpha-acetylenes in said effluent are present in an amount less than about 25 parts per million parts (ppm) by weight of said mixture.

4. The process of claim 3 wherein said reactor is operated at a pressure in the range from about 10 psia (lbs/in$^2$ abs) to about 30 psig (lbs/in$^2$ gauge).

5. The process of claim 4 wherein said conjugated diolefin in said hydrocarbon vapor mixture is isoprene and includes more than about 0.5 percent cyclopentadiene.

6. The process of claim 4 wherein said conjugated diolefin in said hydrocarbon vapor mixture is butadiene and includes methyl acetylene and vinyl acetylene in a combined amount of less than 1% by weight of the butadiene.

7. The process of claim 5 wherein said alpha-acetylenes include up to about 0.1 percent isopropenyl acetylene.

8. The process of claim 4 including discontinuing introduction of said mixture to said reactor when said alpha-acetylene in said effluent are present in a preselectd amount less than about 50 ppm, and regenerating said catalyst.

9. The process of claim 4 wherein said alpha-acetylenes in said hydrocarbon vapor mixture include pentenynes present in an amount up to about 0.1 percent, and said effluent is essentially free of said pentenynes.

10. The process of claim 4 wherein the catalyst demonstrates a turnover number in the range from about 100 to about 300.

* * * * *